(12) United States Patent
Murigneux et al.

(10) Patent No.: US 8,013,214 B2
(45) Date of Patent: Sep. 6, 2011

(54) MAIZE HAVING AN IMPROVED DIGESTIBILITY

(75) Inventors: Alain Murigneux, La Roche Blanche (FR); Jean-Pierre Martinant, Vertaizon (FR); Christophe Tatout, Feurs (FR)

(73) Assignee: BIOGEMMA S.A.S., Paris (FR)

( * ) Notice: Subject to any disclaimer, the term of this patent is extended or adjusted under 35 U.S.C. 154(b) by 842 days.

(21) Appl. No.: 11/664,171

(22) PCT Filed: Sep. 28, 2005

(86) PCT No.: PCT/EP2005/054885
§ 371 (c)(1),
(2), (4) Date: Mar. 29, 2007

(87) PCT Pub. No.: WO2006/035045
PCT Pub. Date: Apr. 6, 2006

(65) Prior Publication Data
US 2009/0031439 A1    Jan. 29, 2009

(30) Foreign Application Priority Data
Sep. 29, 2004 (FR) ................................. 04 10297

(51) Int. Cl.
*A01H 5/10* (2006.01)
*A01H 5/00* (2006.01)
*C12N 15/00* (2006.01)

(52) U.S. Cl. ..... 800/291; 800/278; 800/295; 800/300.1; 800/260; 800/275

(58) Field of Classification Search ........................ None
See application file for complete search history.

(56) References Cited

FOREIGN PATENT DOCUMENTS

| EP | 0516958 A2 | 12/1992 |
|---|---|---|
| WO | WO-93/05160 A1 | 3/1993 |
| WO | WO-97/12982 A1 | 4/1997 |
| WO | WO-99/24561 A2 | 5/1999 |

OTHER PUBLICATIONS

U.S. Appl. No. 12/447,023.
U.S. Appl. No. 12/447,086.
U.S. Appl. No. 12/743,921.
Anterola, A. M. et al., "Trends in lignin modification: a comprehensive analysis of the effects of genetic manipulations/mutations on lignification and vascular integrity," Phytochemistry, 2002, vol. 61, pp. 211-294.
Chen, F. et al., "Evidence for a novel biosynthetic pathway that regulates the ratio of syringyl to guaiacyl resdues in lignin in the differentiating xylem of *Magnolia kobus* DC," Planta, 1999, vol. 207, pp. 597-603.
Matsui, N. et al., "Conversion of guaiacyl to syringyl moieties on the cinnamyl alcohol pathway during the biosynthesis of lignin in angiosperms," Planta, 2000, vol. 210, pp. 831-835.
Pichon, M. et al., "Cloning and characterization of two maize cDNAs encoding cinnamoyl-CoA reductase (CCR) and differential expression of the corresponding genes," Plant Molecular Biology, 1998, vol. 38, pp. 671-676.
Pinçon, G. et al., "Simultaneous down-regulation of caffeic/5-hydroxy ferulic acid-O-methyltransferase I and cinnamoyl-coenzyme a reductase in the progeny form a cross between tobacco lines homozygous for each transgene. Consequences for plant development and lignin synthesis[1]," Plant Physiology, 2001, vol. 126, pp. 145-155.
Poke, F. S. et al., "Sequence variation in two lignin biosynthesis genes, cinnamoyl CoA reductase (CCR) and cinnamyl alcohol dehydrogenase 2 (CAD2)," Molecular Breeding, 2003, vol. 12, pp. 107-118.
Raina, S. et al., A collection of sequenced and mapped Ds transposon insertion in *Arabidopsis thaliana*, Plant Molecular Biology, 2002, vol. 50, pp. 93-110.
Ralph, J. et al., NMR characterization of altered lignins extracts from tobacco plants down-regulated for lignification enzymes cinnamylalcohol dehydrogenase and cinnamoyl-CoA reductase, Proc. Natl. Acad. Sci. USA, 1998, vol. 95, pp. 12803-12808.
Vignols, F. et al., "The brown midrib3 (bm3) mutation in maize occurs in the gene encoding caffeic acid O-methyltransferase," The Plant Cell, 1995, vol. 7, 407-416.
Yamauchi, K. et al., Multiform biosynthetic pathway of syringyl lignin in angiosperms, Planta, 2003, vol. 216. pp. 496-501.
Abstract in English language for EP0516958 (from Espace), 1992.

*Primary Examiner* — Brent T Page
(74) *Attorney, Agent, or Firm* — Connolly Bove Lodge & Hutz LLP

(57) ABSTRACT

The invention relates to a maize plant having a decrease in the CCR enzyme activity due to the presence of the 3318 allele and its use for ensilage.

5 Claims, 2 Drawing Sheets

MAIZE HAVING AN IMPROVED DIGESTIBILITY

RELATED APPLICATIONS

This application is a national stage application (under 35 U.S.C. 371) of PCT/EP2005/054885 filed Sep. 28, 2005, which claims the benefit of French application 04 10297 filed Sep. 29, 2004.

The present invention relates to the field of plant improvement, in particular of plant improvement by modification of the quality and/or of the quantity of lignin. Given the qualitative importance of lignin, an increase, a decrease or a modification of the quantity and/or of the quality of lignin can have considerable industrial or agronomic consequences. The present invention relates more precisely to the development of a specific allele of the gene encoding the first isoform of cinnamoyl CoA reductase or CCR1 (EC: 1.2.1.44) in maize. The presence of this allele results in a decrease in the quantity of lignin present in the plant.

Lignin is one of the two main components of the plant wall, with cellulose. The plant wall consisting mainly of cellulose, hemicellulose and lignin provides the cell with a natural barrier against the outside. In fact, many studies have demonstrated that one of the responses to biotic stresses (pathogenic attacks) or abiotic stresses (drought, wind, etc.) consists of a strengthening of the plant wall, in particular of a higher lignin content. Moreover, many agronomic or industrial sectors find that their yields are directly linked to the lignin content and/or composition of the wall. Among them, it is possible to mention paper industries, fuel production or the production of ensilage.

Consequently, it is advantageous to be able to modulate the lignin content and composition either in order to strengthen plant walls so as to improve the resistance to stresses or, on the contrary, to weaken the plant wall in order to facilitate extraction of cellulose or of other chemical compounds (paper industry, energy production) or the digestibility of fodder (Baucher et al., 1998 Plant Mol Biol 39, 437-447).

For example, improving the qualities of maize for ensilage consists in decreasing the lignin content or in modifying the composition thereof. Maize ensilage is a foodstuff of value: the yield in the field is relatively high, harvest and storage are easy, the nutritional qualities are stable and can readily be supplemented with proteins by means of other fodder ensilages or by means of soya bean cakes. An experiment carried out by Emile (1995, Annales de zootechnie) demonstrates that a more digestible variety makes it possible to increase the level of milk production by more than one kilogram per day, and to increase the weight gain by cows by 22 kg, compared with a less digestible variety. Thus, the more digestible the variety, the higher the milk production and the smaller the loss of meat content. Optimization of the qualities of maize ensilage thus consists in increasing the net energy provided by this type of foodstuff by improving its digestibility and therefore by decreasing the lignin content.

Thus, the selecting or obtaining of more digestible maize plants, in which the lignin biosynthetic pathway is modified, that have good yields and are not very sensitive to various stresses (mechanical, water-related, etc.) is one of the favoured approaches for improving maize.

However, it is difficult to know how to modify the lignin biosynthetic pathway and to predict the consequences of this or that modification. In fact, the lignin biosynthetic pathway is a complex pathway, that has not been completely elucidated and that involves a large number of enzymatic reactions (Dixon et al., 2001, Phytochemistry, 57(7), 1069-1084).

Lignin is considered to be an insoluble polymer of 3 monomers of alcohols or monolignols: p-coumaryl alcohol (H subunits), coniferyl alcohol (G subunits) and sinapyl alcohol (S subunits), derived from the phenylpropanoide pathway (Neish, 1968, Constitution and Biosynthesis of lignin, Eds New York, Springer Verlag 1-43). Each type of precursor can form a variety of linkages with others, and thus constitute lignin. Other linkages can also be established with other parietal compounds (polysaccharides and proteins) so as to form a complex three-dimensional network.

The main steps are hydroxylation thereof, O-methylation of the aromatic rings and then conversion of the carboxyl side chain to an alcohol function.

The current hypothesis for the biosynthetic pathway of monolignols considers that the metabolic network resulting in the formation of the S and G subunits involves successive reactions consisting of hydroxylations and of O-methylations at various levels of oxidation of the side chain. The enzymes of the network include:

- different O-methyltransferases: caffeic acid 3-O-methyltransferase (COMT), 5-hydroxyconiferyl aldehyde O-methyltransferase (AldOMT) and caffeoyl coenzyme A 3-O methyltransferase (CCoAOMT),
- hydroxycinnamate coenzyme A ligases (4CL),
- a cytochrome P450-dependent ferulate 5-hydroylase (F5H),
- and several isoforms of cinnamoyl Co A reductase (CCR) and of cinnamyl alcohol dehydrogenase (CAD).

The properties of these various enzymes have been the subject of reviews (Boudet et al., 1995 New Phytol. 129, 203-236; Dixon et al., 2001, mentioned above; Whetten et al., 1998 Annu Rev. Plant Physiol Plant Mol Biol, 49, 585-609, Li et al., 2000 J. Biol Chem, 275, 6537-6545).

For several years, scientists have attempted to modify the lignin contents and composition of plants by overexpressing or underexpressing one or more genes of the lignin biosynthetic pathway (Anterola and Lewis, 2002, Phytochemistry 61, 221-294). In particular, patent applications WO 99/24561, EP 0 516 958, WO 93/05160 and WO 97/12982 disclose the various strategies envisaged. However, the overexpression or the underexpression of one or more enzymes does not always give constant and predictable results. For example, the inhibition of CCR would have serious or even harmful physiological consequences, in particular on the vascular system of the plant (Pinçon et al., 2001, Plant Physiol. 126, 144-155). It appears that the phenotype of the transformant is very different depending on the degree of inhibition of CCR. A CCR antisense tobacco line for which the residual activity is 6% will have a small phenotype with spoon-shaped leaves, whereas another tobacco transformant for which the residual CCR activity is 9% will have a normal phenotype. Thus, compensation phenomena are thought to exist within the lignin biosynthetic pathway. Consequently, while it is known that the inhibition of CCR causes a decrease in the quantity of lignin, it is very difficult for those skilled in the art to predict what the consequences will be from the phenotypic point of view and from the point of view of the quality of lignin. Some authors have shown that the inhibition of CCR causes the incorporation, into the lignin, of unusual compounds such as tyramine ferulates (Ralph et al., 1995, PNAS, 95 (22) 12803-12808). However, this compensation with unusual phenols appears to be questionable (Anterola et al., 2002, Phytochemistry, 221-294).

Another strategy consists in using natural mutants in the varietal selection schemes. For example, the natural maize mutant bm3 has an insertion in the gene encoding COMT-AldOMT and thus has excellent digestibility. These bm3 maize plants differ from the "normal" maize plants in terms of a greatly reduced (up to 40%) lignin content, but their yield in the open field is less. They are, in addition, more sensitive to increased lodging (breaking, bending over or falling of the plant) and show a lack of growth and of vigour at the beginning of vegetation, and delayed flowering. All these deficiencies prevent the exploitation thereof (Barrière and Argillier, Agronomie, 13, 865-876 (1993)).

Cinnamoyl coenzyme-A reductase acts, in the lignin biosynthetic pathway, to convert p-coumaroyl CoA, feruloyl CoA and sinapoyl CoA to aldehydes. The existence of these three substrates either implies that several isoforms of CCR exist or that CCR(s) is(are) capable of catalyzing the reactions from a large variety of substrates (Lewis and Yamamoto, 1990, Annual Review of Plant Physiol. And Plant Mol Biol 41, 455-497; Davin and Lewis 1992, In Stafford H A Ibrahim R K (Eds), Phenolic Metabolism in Plants, Vol. 26, Plenum Press, New York and London, 325-375; Lewis et al., 1999, In Barton D. H. R., Sir, Nakanishi, K., Mehcohn, O. Eds, Comprehensive Natural Products Chemistry, Vol. 3, 617-745). Another hypothesis envisages different CCR isoforms according to cell type (Chen et al., 1999, Planta, 207, 597-603; Matsui et al., 2000, Planta, 210, 831-835). However, none of these hypotheses has been clearly proved.

To date, two isoforms of CCR have been isolated in maize (Pichon et al., 1998, Plant Mol Bio, 38, 671-676). It would appear that only CCR1 is involved in the lignin biosynthetic pathway.

Patent applications WO 97/12982, WO 98/39454 and WO 99/10498 concern, inter alia, the maize CCR gene. These applications do not describe how to obtain maize plants with improved digestibility, having a mutated CCR gene. Those skilled in the art, without a precise description of the production of a maize plant with improved digestibility, is incapable of predicting the effect produced on the maize by inhibition of its CCR. In fact, given the complexity of the phenomenon resulting in lignification, those skilled in the art cannot use results obtained on other plants as a basis, since it is becoming increasingly clear that the biosynthetic pathways differ from one angiosperm species to another (Yamauchi, 2003, mentioned above). In addition, it is evident that there are phenomena of cross compensations and/or regulations between genes in this biosynthetic pathway (Pinion et al., 2001, op. cit.). Consequently, if those skilled in the art do not have precise information (species, enzyme targeted, implementation of the transformation, etc.) regarding the production of plants with improved digestibility, they are incapable of predicting whether the effects of this transformation will be in accordance with those desired. In addition, there is no natural mutant in which CCR is affected that could be used by selectors. Similarly, it can be readily envisaged that not all mutant alleles will have the same effect on the plant; specifically, modifications in the sites responsible for regulating expression of the gene may result in a modification of the spatiotemporal profile of the presence of the corresponding enzyme.

An object of the present invention is to provide those skilled in the art with a maize that effectively has improved digestibility, by developing a favourable allele of CCR1 (called Δ 3318), an insertion having been made in the first intron of the gene encoding this enzyme, the sequence of an allele of which is represented by SEQ ID No. 1. The sequence of the corresponding mRNA is GenBank X98083 (SEQ ID No. 2), the coding portion being nucleotides 79 to 1194. It is clear that the sequences are only given by way of examples, and that those skilled in the art are capable of identifying themselves the CCR1 genomic and/or mRNA sequences for various maize varieties.

For example, another allele corresponding to the maize CCR sequences is represented by accession number Y13734 (GenBank).

The invention also relates to a maize cell which contains the Δ 3318 allele (homozygous or heterozygous).

Seeds having the Δ 3318 allele were deposited with NCIMB Limited, 23 St Machar Drive, Aberdeen, Scotland, AB24 3RY, UK, on 23 Jul. 2004, according to the provisions of the treaty of Budapest, under the number NCIMB 41236.

The invention provides in particular a maize plant having said Δ 3318 allele. Despite the presence of the insertion in an intron, this plant shows a decrease in the activity of the CCR1 enzyme, such that the lignin content is decreased by at least 5%, preferably by at least 7%, more preferably by at least 10%, and the amount of S subunits is increased by at least 10%, preferably by at least 12%, more preferably by at least 16%, compared with virtually isogenic plants that do not have this allele resulting in such an inhibition of the CCR1 activity.

Thus, the present invention relates in particular to a maize plant exhibiting an increase in digestibility (measured by NIRS) of at least 10%, preferably of at least 15%, more preferably of at least 20%.

Preferably, the maize according to the invention is an "elite" maize. Those skilled in the art are perfectly aware of the definition of an elite maize. The term "elite maize" means a maize intended to generate hybrids intended to be marketed, by crossing with another elite maize. An elite maize is defined as such in relation to the territory envisaged for the marketing, and also the agronomic characteristic(s) desired for the hybrid progeny. It is in particular a maize that can be listed in a reference catalogue.

Thus, depending on whether the progeny are intended for human or animal food, a seed yield, or a yield per hectare and good digestibility will, for example, be respectively sought when evaluating the "elite" nature "of the maize".

In order to determine the elite nature of a maize, hybrids obtained from this maize are compared with reference commercial hybrids (sold for the same purpose in the same region), by means of field trials, and by means of reading and measurements of agronomic characteristics appropriate to the desired objective. A maize is defined as elite if the results obtained for the parameters studied for a hybrid obtained by crossing of said maize are 90% superior to the results recorded for the same parameters of the reference hybrids. In the context of the present invention, the digestibility characteristic (digestibility measured by NIRS (near infrared spectroscopy), for example) is in particular studied.

Near infrared spectroscopy (NIRS) is the measurement of the wavelength and the intensity of absorption of near infrared light by a sample, in the 800 nm-2.5 μm (12500-4000 $cm^{-1}$) range. This spectroscopy is typically used for quantitative measurements of organic functional groups, in particular O—H, N—H and C═O. This method is commonly used for analysing the digestibility of samples.

Thus, an elite maize is a maize that combines the maximum number of agronomic characteristics required for economic penetration of the market targeted. Since the maize market is today a market of hybrids, the elite nature of a maize is also evaluated in terms of the capacity of said maize for hybrid combination/production.

Thus, the present invention preferably relates to an elite maize intended for the marketing of hybrids for animal feed and ensilage (silage), that has the Δ 3318 allele. This elite maize is therefore homozygous for the Δ 3318 allele.

In another embodiment, the invention relates to a hybrid maize obtained by crossing two homozygous parent lines, said hybrid maize having a Δ 3318 allele. This hybrid maize can be homozygous (if each homozygous parent has the Δ 3318 allele) or heterozygous for the Δ 3318 allele.

The present invention also provides those skilled in the art with the means for selecting the maize plants having this improved digestibility characteristic. It is in fact sufficient to perform a PCR or Southern Blotting (hybridation of genomic DNA on a membrane) in order to follow the presence of the insertion in the first intron of the gene encoding CCR1. Those skilled in the art can readily determine the primers and probes for identifying the presence of the Δ 3318 allele.

A subject of the invention is also a method for obtaining maize plants having improved digestibility by virtue of the Δ 3318 allele.

The invention also relates to a method for obtaining a maize line having increased digestibility, comprising the step consisting in introgressing the Δ 3318 allele in a reference line having an agronomic quality characteristic. The introgression of the characteristic is in particular carried out by selection, according to methods known in the art (crossing and self-pollination). The plants are in particular selected using molecular markers.

The principle thereof is recalled below:

A series of back crosses are performed between the elite line and the line carrying the Δ 3318 allele (single site on chromosome 1).

In the course of the back crosses, the individuals carrying the Δ 3318 allele and having recombined the smallest fragment from the donor line around this allele can be selected. Specifically, by virtue of molecular markers, the individuals having, for the markers closest to the gene, the genotype of the elite line are selected.

In addition, it is also possible to accelerate the return to the elite parent by virtue of the molecular markers distributed over the entire genome. At each back cross, the individuals having the most fragments derived from the recurrent elite parent will be chosen.

With correct implementation, as early as the fourth generation, a virtually isogenic line of the elite line, i.e. identical to the starting elite line but having integrated the locus carrying the Δ 3318 allele, can be obtained.

Thus, in a preferred embodiment, said method comprises the steps consisting in:
 a) crossing a first maize line that has the Δ 3318 allele with a second maize line that does not have said allele,
 b) genotyping the progeny obtained and selecting the descendants having the Δ 3318 allele that have the best genome ratio as regards said second line,
 c) performing a back cross of said descendants with said second maize line,
 d) repeating, if necessary, steps b) and c) until an isogenic line of said second maize line, having the Δ 3318 allele, is obtained,
 e) optionally, performing a self-pollination in order to obtain a plant that is homozygous for the Δ 3318 allele.

It is recalled that a "isogenic" line (to another line) according to the invention is a line only differing from said another line at very few loci (less than 20, more preferably 10), and differing at the CCR allele, one carrying the Δ 3318 allele according to the invention and the other not. This line has also been called "virtually isogenic", in the context of this invention.

The genotyping in step b) is preferably carried out using molecular markers (microsatellite markers, for example) that make it possible to define the part from each of the two parents in the progeny. The maize plants, in the progeny, that have the appropriate genetic characteristic as regards the Δ 3318 allele are also selected, in a conventional manner, by means of molecular biology methods (such as PCR or Southern blotting).

Surprisingly, it has been shown that repeating the back crosses between the lines selected in step b) and the second maize makes it possible to obtain the appearance of a much more marked phenotype in said second maize.

This result is entirely surprising since one could have expected to observe an increase in digestibility from the first cross of the maize having the Δ 3318 allele with the second maize.

Thus, those skilled in the art could not obtain maize exhibiting increased digestibility by following the teaching of applications WO 97/12982, WO 98/39454 and WO 99/10498, or be prompted to develop a specific allele, moreover having an insertion in an intron.

By using the teaching of these applications, which do not mention the importance of performing certain back crosses and, optionally, self-pollinations, those skilled in the art could have come to the conclusion that CCR1 had no role in terms of improving digestibility in maize.

In particular, none of these applications either describes or suggests the allele according to the invention, or even the possibility of developing it.

Finally, the invention relates to the use of a maize according to the invention, for preparing a composition intended for livestock feed, to a method for preparing a composition intended for livestock feed, comprising the ensilage of a maize according to the invention, and also to the composition intended for livestock feed, thus obtained.

EXAMPLES

Description of a Maize Having an Alteration in the CCR Gene

A maize line having an insertion of the mutating element in the first intron at position 632 of the reference sequence SEQ ID No. 1 is isolated. The allele thus obtained is called Δ 3318.

Although present in an intron, it is assumed that this insertion results in a deregulation of the transcription and/or the translation of the CCR1 gene, or of the stability of the CCR1 mRNA, leading to a decrease in the activity of the enzyme in the presence of the Δ 3318 allele, as attested to by the biochemical results with respect to ligand composition and content (see below).

In order to determine whether the insertion is in homozygous or heterozygous form, a pair of primers was defined: a sense primer CCR 15 of sequence SEQ ID No. 3: GTA-CATCGCCTCGTGGTTAG and an antisense primer CCR 14 of sequence SEQ ID No. 4: GAGTTCTGCAAGAGAAC-GAG.

In addition to these two primers, the primer OMuA SEQ ID No. 5: ATCGACAAATATATATGTTTATAAGG, specific for the TIR (terminal inverted repeat) regions of the endogenous transposable element, is used. This primer is directed towards "the outside" of the transposon.

Figure 1:
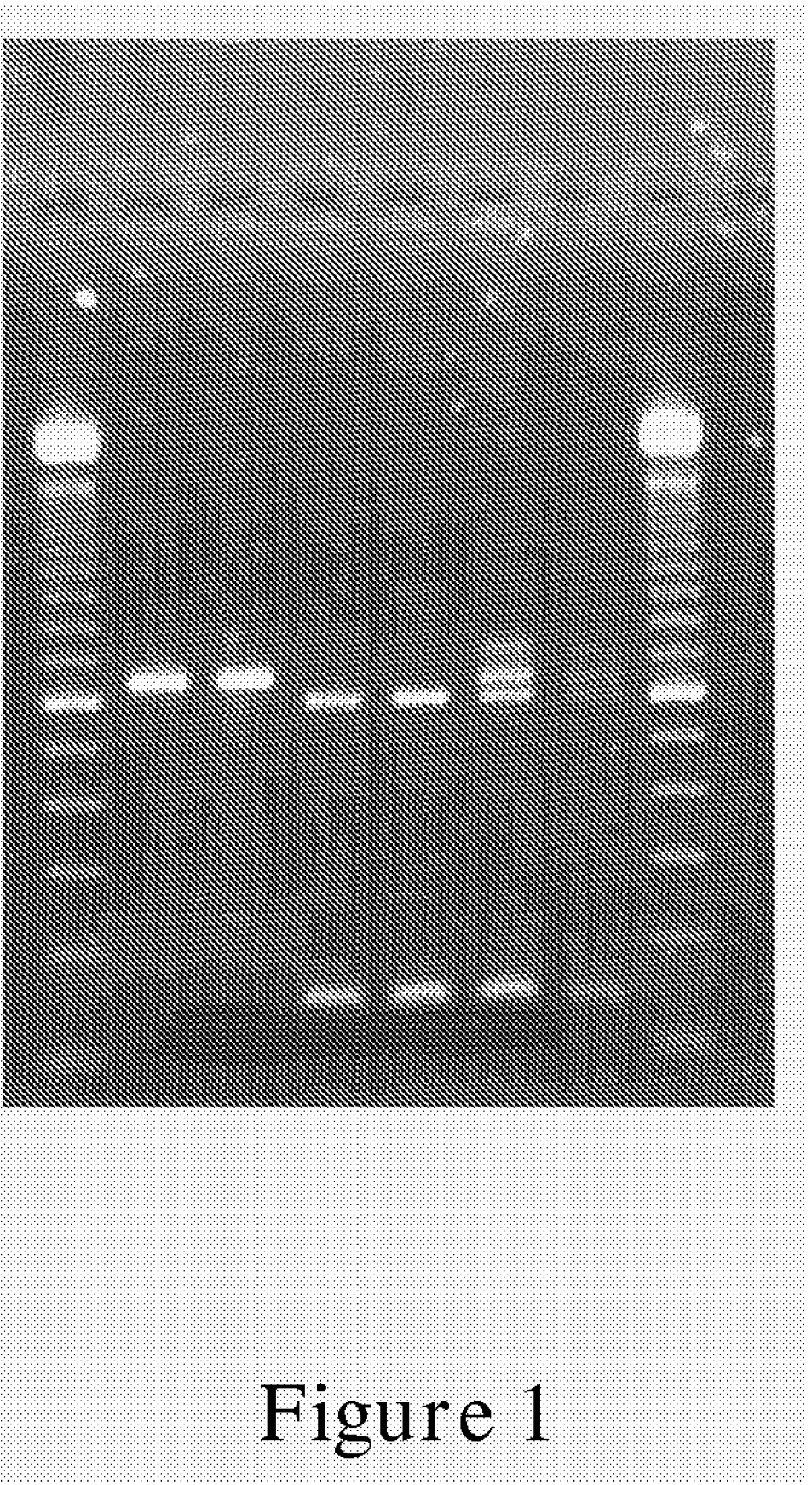
FIG. 1: illustration of a method for following the Δ 3318 allele. Amplification results.

These three primers can be used simultaneously in an experiment comprising PCR amplification from genomic DNA (hybridization temperature=58° C.). Loading of the amplification products onto a gel reveals:
- that a single band approximately 630 pb long is obtained for plants referred to as wild-type at this locus (i.e. not having the mutation);
- that two bands of approximately 115 pb and 565 pb are obtained for mutant homozygous plants, corresponding to the amplifications obtained with the primers present in the gene and in the transposon (due to the insertion, amplification with the primers CCR 15 and CCR 14 is impossible (too long));
- or that all three bands are obtained for heterozygous plants. These results are given in FIG. 1.

The first and the last wells on the gel contain the size marker: the lowest band corresponds to 100 pb and there are 100 pb between each band.
Wells 2 and 3 correspond to wild-type individuals.
Wells 4 and 5 correspond to mutant individuals.
Wells 6 and 7 correspond to heterozygous individuals.

One can also use the three primers SEQ ID No 3, SEQ ID No 6 (antisense CCR primer CTGGTTTTCTCGCAGAACTC) and SEQ ID No 7 (primer within the le transposon CTTCGTCCATAATGGCAATTATCTC).

Scheme for the Back Crosses and Self-Pollinations

In order to study more precisely the effect of the insertion observed in the first intron of CCR in an elite maize, successive back crosses are carried out with a Limagrain elite line.

This method makes it possible to very rapidly obtain virtually isogenic lines that differ only in terms of the locus carrying the modified allele, the descendants being tested for the presence of a genome ratio as close as possible to that of the elite parent while at the same time having the allele that it is desired to introgress. These tests are aided by molecular markers (well-known techniques, microsatellites, AFLP, etc.). In order to try to assess the effect of the insertion at the earliest moment (production of homozygous plants), self-pollinations are carried out at the various intermediate stages of back cross.

Figure 2:
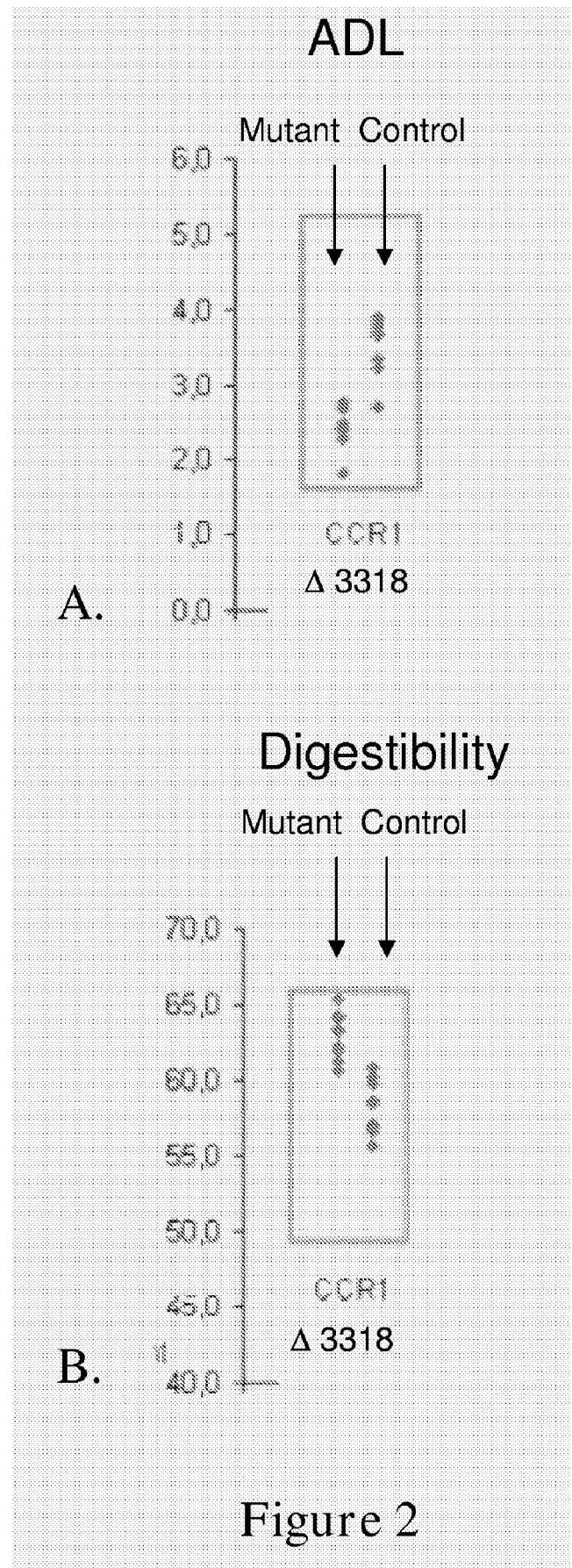
FIG. 2: NIR results of the introgression of the Δ 3318 allele on the quantity of lignin (FIG. 2.A) and the digestibility (FIG. 2.B). Mutant: plants having the Δ 3318 allele; control: plants not having this allele.

FIG. 2 gives NIR results obtained on BC2S2 plants (2 back crosses and 2 self-pollinations).

This shows that the introgression of the Δ 3318 allele makes it possible to obtain a decrease in the quantity of lignin (Acid Detergent Lignin) after isolation of the walls (Neutral Detergent Fibres), according to methods known to those skilled in the art (FIG. 2.A), and an improvement in the digestibility of the organic matter of the stem+leaves portion of the plant, as a percentage of digested organic matter (FIG. 2.B).

It is also possible to measure the percentage of Klason lignin and the wall digestibility, according to methods that are known in the art, which gives the following results for the BC2S2 maize plants:

|  | Value for the mutant | Value for the control |
|---|---|---|
| % lignin in the walls | 15.7 | 16.7 |
| Wall digestibility | 25 | 21 |

The invention claimed is:

1. A method for obtaining a maize exhibiting increased digestibility, comprising the step of introgressing the Δ 3318 allele into said maize.

2. The method according to claim 1, comprising the steps:
a) crossing a first maize line that has the Δ 3318 allele with a second maize that does not have said allele,
b) genotyping the progeny obtained and selecting the descendants having the Δ 3318 allele that have the best genome ratio as regards said second maize,
c) performing a back cross of said descendants with said elite second maize line that can be used for the production of hybrids,
d) repeating, if necessary, steps b) and c) until an isogenic line of said second maize, having the Δ 3318 allele, is obtained,
e) optionally, performing a self-pollination in order to obtain a plant that is homozygous for the Δ 3318 allele.

3. A maize plant having the Δ 3318 allele of the CCR1 gene, wherein said Δ 3318 allele of the CCR1 gene comprises an insertion of a transposon in the first intron of the CCR1 gene, said insertion being located at position 632 of reference sequence SEQ ID NO: 1 representing an allele of the CCR1 gene, said Δ 3318 allele being present in a representative sample of seeds deposited with NCIMB under the number NCIMB 41236.

4. A method for preparing a composition intended for livestock feed comprising the step of preparing silage with the maize according to claim 3.

5. A maize seed having the Δ 3318 allele of the CCR1 gene, wherein said Δ 3318 allele of the CCR1 gene comprises an insertion of a transposon in the first intron of the CCR1 gene, said insertion being located at position 632 of reference sequence SEQ ID NO: 1 representing an allele of the CCR1 gene, said Δ 3318 allele being present in a representative sample of seeds deposited with NCIMB under the number NCIMB 41236.

* * * * *

SEQUENCE LISTING

```
<160> NUMBER OF SEQ ID NOS: 7

<210> SEQ ID NO 1
<211> LENGTH: 6080
<212> TYPE: DNA
<213> ORGANISM: Zea mays
<220> FEATURE:
<221> NAME/KEY: insertion
<222> LOCATION: (632)..(633)
<220> FEATURE:
<221> NAME/KEY: misc_feature
<222> LOCATION: (2744)..(2747)
<223> OTHER INFORMATION: n is a, c, g, or t
<220> FEATURE:
<221> NAME/KEY: misc_feature
<222> LOCATION: (2845)..(2846)
<223> OTHER INFORMATION: n is a, c, g, or t

<400> SEQUENCE: 1
ggggccacac cacacccaca ccgcgcgagc gcgcacggtg tccggacgtc tattatcatc      60
tcgctgtccg tgtctgtctc agcgctactc atcactcgct cgcatcgcac tgcgcgctcc     120
gatccccctc caccgtctc  agctagcagc ctcgccttgt tgtggcctat aaattccgcg     180
ccactccaac gcccacccttc ctcaggatga atcggaagag agaatcctac caaacctagc    240
taccaactcg atcgtcgtca tcacgctcga ccgcacaact gcaccaaggg gggaggagac    300
ctaaaaacta ctacatcttt tagctacaca tctagctaaa gatcgagagg ggtaaataag    360
gacgagcggg cgcgagctag aagagcagct gcaggtacta ccatcatcgt cgtcgtcgtc   420
gccaggatga ccgtcgtcga cgccgtcgtc tcctccaccg atgccggcgc ccctgctgcc    480
gccgccaccg cggtaccggc ggggaacggg cagaccgtgt gcgtgaccgg cgcggccggg    540
```

```
tacatcgcct cgtggttggt gaagctgctg ctcgagaagg atacactgt gaagggcacc      600
gtcaggaacc caggcatgca tgcctcctgc ttgttgttat atataagcag tctactatgt     660
cgacctgcgc gagcgtggca gcagatggag cgattaacgt gtttgtacat gttcatggca    720
gcagatgacc cgaagaacgc gcacctcaag gcgctggacg gcgccgccga gcggctgatc    780
ctctgcaagg ccgatctgct ggactacgac gccatctgcc gcgccgtgca gggctgccag    840
ggcgtcttcc acaccgcctc ccccgtcacc gacgacccgg tgagttccgt cggccgggtt   900
agttccagca ctcgtcgact gactgatcag taaagtagta acaaggggac cgcatgcacc    960
atgcatgtgt gcgcgtgcag gagcaaatgg tggagccggc ggtgcgcggc accgagtacg   1020
tgatcaacgc ggcggcggag gccggcacgg tgcggcgggt ggtgttcacg tcgtccatcg   1080
gcgccgtgac catggacccc aagcgcgggc ccgacgtcgt ggtcgacgag tcgtgctgga   1140
gcgacctcga gttctgcgag aaaaccaggg tgggtgtgct tgcttgctca cttttatttg   1200
atcgatcgtc tccatccatc catcatctga tctactacta agtacagtag cttgtagcta   1260
gctcctgcta taccgtccgc tgcaccacgt acgccagcac catatattaa attagtgttt   1320
ccgatccttt aatttgatgc atacgttttc atttcttgca agtaaggacg atcaaaggaa   1380
agggtgaaag aaacactaat aaaggtagct gtgacgagat aggcgaatca ttacctgcta   1440
gtatattggc atgcatgcac tagctagcta ccaaccaccg agagccctag aagagactag   1500
actagagtac gttcgagtac ttttgaggcc gccaaataga accaactaag tgctcatcgt   1560
catcgatggt gcctgtccaa agcacacaga gagcagcact agctagctag gatttgaacc   1620
acagcttttt ctagcgtgac caacagcact agctaggcaa gcagccgaaa taacgcatat   1680
atatgaaaag gaatttggtt ccgcaaaaaa aaaacggag aacggaaaag gagcaaatca    1740
tgcatgtgga cggagaacgc acgcaccacg cgaattaatc ctgcctctgc atgggccac    1800
gcacgccgtc gccgatggac acatgtatgg catgcagcgc ttgagctacg acctgcttaa   1860
ttatcagtag cgaagaatct catcccacat gcgtgtttct tcaacacgta cgcatggaca   1920
ctctttagtg tcaaagctaa agctgagaat tcaaattaac cttgctattt tgatcgcggt    1980
gggctcttaa aatgattgga cagatgcagc accgtaccca cgccttacaa ctctcctagc   2040
tagctagccg ccccgcaacc acactagaat tgttctagcc tagtagcctg tgtctgtgtc    2100
tgtgtgtgcg tgtagcgtgt cctatggaag acggaaattt cagctgccca gaaaaacaca   2160
cacatgcacg acgacgacgc caccagtttg ccggtcgaca catgctagca gtgatgggca   2220
ggcctttgtc gatcgccatt tattctgtgc agcaaactct gctggcttta atttgcggag   2280
gagcgagcaa attctactct ccccggcttt aatttgcgga tttattacaa gtcgtcatcc   2340
caacttcatt ggaccaactt ttatagaata tttttattta aaaaaaactg tagtaattta   2400
cgatatcaaa cgagtaatac tatattttt attaattgtg tttttatagt gtatttattt    2460
gatggcatgt ttttttttgc tcctatagtt ttagttaaat ttgatgtgct accttgacc    2520
cactaataat atttttaaaa aaatgattta taattctgaa ccgagggaag gattttatat   2580
atatatatat atatatatat atatatatgg caacgtatcc tgtgtaaaag gttctccagt   2640
gtaaatatgc taaatgcct taacaacctt tggatccaga atcaaaggct aattttaatc   2700
ctacctaacc gccaccgcac cagattacca ggaggggggtt cttnnnnaaa aacacaagat  2760
tatcaggtgg gattaagatt agccctttgaa tctggatcca aaggttgtta agacgtttta   2820
gcatgtttac acaggagaac ctttnnacag gagacgttgc ccctctctct ctctctctct   2880
ctctctctct ctctctatat atatatatat atatatatat atatatatat atatatatat   2940
```

```
atggtacgac tttggtgggt cgctcgtcgc ctctcccgac ggcccaacct ccaaccaacg    3000
caaaatttac ttgcattgca tggccgccat cctcattatt tttttgtctg tttctgacgc    3060
aacaatcacg tcagcatgac acacagcata tatcattact gtgttctaag tgcacgccca    3120
taacgcatat gcacgctgca gaactggtac tgctacggca aggcggtggc ggagcaggcg    3180
gcgtgggaga cggcccggcg gcggggcgtg gacctggtgg tggtgaaccc cgtgctggtg    3240
gtgggccccc tgctgcaggc gacggtgaac gccagcatcg cgcacatcct caagtacctg    3300
gacggctcgg cccgcacctt cgccaacgcc gtgcaggcgt acgtggacgt gcgcgacgtg    3360
gccgacgcgc acctccgcgt cttcgagagc ccccgcgcgt ccggccgcca cctctgcgcc    3420
gagcgcgtcc tccaccgcga ggacgtcgtc cgcatcctcg ccaagctctt ccccgagtac    3480
cccgtcccag ccaggtctga tttcatagta ctcattgctt gcttgcttgc ttaggaaccg    3540
gtggatagga atccactggt ggtattaatt aggtgacgcg agcaattaag caaagcgtgg    3600
tagtactcgt actacactgc aaattaaact ccggtggatc ccagcgtagt aggtgaacga    3660
tggacagggc ccggccggtc acttacgcgt acactgctcg atccacctca tcggccggct    3720
cttgtgctgc acacgaaagc aaagcggccg tcagctgaag aagggcgaac gtatgggggg    3780
cggttcaggt gaaccactct tttgtgtgta tcatcactga cgctgacact ggctagagcg    3840
cgtcctgtgc aagctagcta gttggtagac gcggctagta cacaccacac gccaccaata    3900
tttgcatgct agtgcaagtc agctagctag ctagctagct cacggcggtg gccaatactc    3960
tagacctcaa ttactgccac acgaagcggt agctagatag agtacgtgcg accacttcga    4020
aacgtatctg tccggagcgg tagaaatctg tagcgtacgt cagcgtcgtc tcggagacgg    4080
agaagtagcg tgtagctact attatactac gcgtactaga tgccatccgt gttcgctttg    4140
gccaatcggg gcaaggccgt ttttctgcca tacatcacgt cgtcatcgcc gtcaccacca    4200
ttcgtgactt gtgtagtagg tagtagtata cccggaggcc ggagcagatg catttgctcg    4260
cgtctgcgtt ttgtgctgca acctgcaacc atgtcacagc tgctagctgt tcggttcctc    4320
cgttgcaggc ctgcgtgtgc catgtggagc agagagttgg gttctttcta cctagcacta    4380
taagagaaac cgctcggtca cggaggtaca ggcaacgcac gtatgtctag aacttaactt    4440
ctcgaatatt tgtcgaccac tagtttattt tttttaacta aaacgcgata aataaaaaaa    4500
acaaagaaat actagtttct atcaagtaag cagcttaatc aaatctacga aacagaggaa    4560
ggaacgccgc agaaacttcc taggaatttt cttcatcaac tcgcagcaaa tttattttc     4620 ttcaggcttg gtggggagg gggtgacctc tgcgqtaggt catctccaag gtcctaccta    4680
gatcgatcat catttaccac acaagaagta accatgcatg catctctctt accacatcat    4740
tacatgtaga ataagaatat tggcgagtca tgcaagcatc tattacgaaa catgtagaat    4800
atttacacta ctactccacc atccggtatt ttcaaacaaa gaacatgcat gggcaagaaa    4860
aggtcagttt cgctcgactg ctgactgcaa gatgatcttt accaaccgac ctctaatcac    4920
gcgatggaat attcaacttc ccgattcgac ggcggcgggc aatcctggtt gtaacagccg    4980
tggactgcaa ctgcaatggg tcctccgtcc gttcgttgtt agtttacggc ttttcccatg    5040
acaaattccg tatgattctt tcaaagatac taccctcctc gtcctcgacc acttgctttg    5100
ctgtcgtaat ctcaccatac caatgaaaac acctagcctt agcgtatgct ctgggccgcc    5160
catgcaagcg ggaagaatct cacctgccca caggacaacc atgtgtttac actagagttg    5220
atcgatactg taactgagaa ccaaaaatga atatgaacga aacggtcttg accttctcgc    5280
tccttttttt tattaggacg accttgactg actgagatcc ttgactgact gtgtgcgtat    5340
```

```
gctattatta gcgtttgctg ctttgcttca ctgactctgt gtgtgtgtgt gagcgcttgg    5400
tgcaggtgct ccgacgaggt gaatccgcgg aagcagccgt acaagttctc caaccagaag    5460
ctccgggacc tggggctgca gttccggccg gtcagccagt cgctttacga cacggtgaag    5520
aacctccagg agaagggaca cctgccggtg ctcggagagc ggacgacgac ggaggccgcc    5580
gacaaggatg cccccacggc cgagatgcag cagggaggga tcgccatccg tgcctgagag    5640
ggcgatgcca cacatgaaca caaagcaatg ttcatactgc tgccctgcac ctgctgtgta    5700
aacaggcctg tgtttgttct ggctgatagt gatgtaccct aagacttgta acgtcatgtt    5760
cgttcttgtg aactatagcg agtgaataaa attggttaat gttggatgtt caaaattttg    5820
cagataagag agtcatcaat tcaggttctg aaaagcaatc ccgaaactac caccctacct    5880
atcccctaca ggctacagta gactgtacaa gaccctttgt taccaaacca aaaaaaaaca    5940
tcggacaaac tcaagactat tcatgttttgg taacctactt gtgtagaaaa gtgagctcta    6000
ttattggctg atgcaatatg ccaacccctta catgcagcag gaaagcaaag aaagaacagt    6060
aaaacaaatg agttggtaaa                                                6080

<210> SEQ ID NO 2
<211> LENGTH: 1398
<212> TYPE: DNA
<213> ORGANISM: Zea mays

<400> SEQUENCE: 2
ggcacgagag gacacaagcg agcgctagcc agaagagcag ctgcaggtac tattatcatc      60
gtcgtcgtcg tcgccaggat gaccgtcgtc gacgccgtcg tctcctccac cgatgccggc     120
gcccctgccg ccgccgccgc accggtaccg gcggggaacg gcagaccgt gtgcgtcacc      180 ggcgcggccg ggtacatcgc ctcgtggttg gtgaagctgc tgctcgagaa gggatacact     240
gtgaagggca ccgtgaggaa cccagatgac ccgaagaacg cgcacctcag ggcgctggac     300
ggcgccgccg agcggctgat cctctgcaag gccgatctgc tggactacga cgccatctgc     360
cgcgccgtgc agggctgcca gggcgtcttc cacaccgcct cccccgtcac cgacgacccg     420
gagcaaatgg tggagccggc ggtgcgcggc accgagtacg tgatcaacgc ggcggcggag     480
gccggcacgg tgcggcgggt ggtgttcacg tcgtccatcg cgccgtgac catggacccc      540 aagcgcgggc ccgacgtcgt ggtcgacgag tcgtgctgga gcgacctcga gttctgcgag     600
aaaaccagga actggtactg ctacggcaag gcggtggcgg agcaggcggc gtgggaggcg     660
gcccggcggc ggggcgtgga cctggtggtg gtgaaccccg tgctggtggt gggcccctg     720 ctgcaggcga cggtgaacgc cagcatcgcg cacatcctca gtacctggcg cggctcggcc     780
cgcaccttcg ccaacgccgt gcaggcgtac gtggacgtgc gcgacgtggc cgacgcgcac     840
ctccgcgtct tcgagagccc ccgcgcgtcc ggccgccacc tctgcgccga gcgcgtcctc     900
caccgcgagg acgtcgtccg catcctcgcc aagctcttcc ccgagtaccc cgtcccagcc     960
aggtgctccg acgaggtgaa tccgcggaag cagccgtaca gttctccaa ccagaagctc    1020 cgggacctgg ggctgcagtt ccggccggtc agccagtcgc tttacgacac ggtgaagaac    1080
ctccaggaga agggccacct gccggtgctc ggagagcgga cgacgacgga ggccgccgac    1140
aaggatgccc ccgcggccga gatgcagcag ggagggatcg ccatccgtgc ctgagagggc    1200
gatgccacac atgaacacaa agcaatgttc atactgctgc cctgcacctg caccttcccc    1260
tgctgtgtaa acaggcctgt gtttgttctg gctgatagtg atgtacccta agacttgtaa    1320
cgtcatgttc gttcttgtga actatagcga gtgaataaaa ttggttaatg ttggatattc    1380
```

```
aaaaaaaaaa aaaaaaaa                                                  1398

<210> SEQ ID NO 3
<211> LENGTH: 20
<212> TYPE: DNA
<213> ORGANISM: artificial
<220> FEATURE:
<223> OTHER INFORMATION: synthetic sense primer CCR 15

<400> SEQUENCE: 3
gtacatcgcc tcgtggttag                                                  20

<210> SEQ ID NO 4
<211> LENGTH: 20
<212> TYPE: DNA
<213> ORGANISM: artificial
<220> FEATURE:
<223> OTHER INFORMATION: synthetic antisense primer CCR 14

<400> SEQUENCE: 4
gagttctgca agagaacgag                                                  20

<210> SEQ ID NO 5
<211> LENGTH: 26
<212> TYPE: DNA
<213> ORGANISM: artificial
<220> FEATURE:
<223> OTHER INFORMATION: synthetic primer OMuA

<400> SEQUENCE: 5
atcgacaaat atatatgttt ataagg                                           26

<210> SEQ ID NO 6
<211> LENGTH: 20
<212> TYPE: DNA
<213> ORGANISM: artificial
<220> FEATURE:
<223> OTHER INFORMATION: synthetic reverse primer CCR

<400> SEQUENCE: 6
ctggttttct cgcagaactc                                                  20

<210> SEQ ID NO 7
<211> LENGTH: 25
<212> TYPE: DNA
<213> ORGANISM: artificial
<220> FEATURE:
<223> OTHER INFORMATION: synthetic primer in transposon

<400> SEQUENCE: 7
cttcgtccat aatggcaatt atctc                                            25
```